United States Patent [19]

Waage

[11] 3,942,529

[45] Mar. 9, 1976

[54] PACKAGE AND METHOD FOR STORING BLOOD

[75] Inventor: Bård Meier Waage, Rosenlund, Sweden

[73] Assignee: Investrop A.G., Zug, Switzerland

[22] Filed: May 25, 1973

[21] Appl. No.: 358,602

Related U.S. Application Data

[63] Continuation of Ser. No. 95,197, Dec. 4, 1970, abandoned, which is a continuation of Ser. No. 695,852, Jan. 5, 1968, abandoned.

[30] Foreign Application Priority Data

Feb. 1, 1967 Sweden.............................. 1459/67

[52] U.S. Cl. ..... 128/272; 128/214 D; 128/DIG. 24; 206/526; 229/3.5 R; 426/106
[51] Int. Cl.² .......................................... A61J 01/06
[58] Field of Search......... 128/214 D, 272, DIG. 24; 206/526; 426/106; 229/3.5; 150/1

[56] References Cited
UNITED STATES PATENTS

| | | | |
|---|---|---|---|
| 3,158,283 | 11/1964 | Rinfret et al. | 220/64 |
| 3,298,597 | 1/1967 | Bellamy | 229/55 |
| 3,425,865 | 2/1969 | Shelton | 117/218 |
| 3,576,650 | 4/1971 | Underwood et al. | 128/272 X |
| 3,645,834 | 2/1972 | McCaffrey | 161/189 |

*Primary Examiner*—Dalton L. Truluck
*Attorney, Agent, or Firm*—Brumbaugh, Graves, Donohue & Raymond

[57] ABSTRACT

A package for storing blood is formed of a plastic laminate with the layer next to the package cavity being formed of a fluorinated ethylene-propylene polymer and the outer layer being formed of a non-thermoplastic polyimide with a melting temperature substantially higher than that of the inner layer. Openings leading to the cavity are heat sealed after blood has been introduced into the cavity by applying heat by conduction near the opening through the outer layer on at least one side of the package for melting and sealing opposing inner layers together. According to the method for storing blood in the package, the package is sealed after blood has been introduced therein by so applying heat through the outer layer and sealing together the opposing inner layers.

6 Claims, 2 Drawing Figures

INVENTOR.
BARD MEYER WAAGE
BY
Brumbaugh, Graves, Donohue & Raymond
his ATTORNEYS.

PACKAGE AND METHOD FOR STORING BLOOD

This application is a continuation of copending application Ser. No. 95,197, filed Dec. 4, 1970, which is a continuation of application Ser. No. 695,852, filed on Jan. 5, 1968, both now abandoned, which claimed priority based on Swedish patent application No. 1459/67 which was filed on Feb. 1, 1967.

BACKGROUND OF THE INVENTION

This invention relates to packages for storing blood and to the method for storing blood in such packages, and more specifically to a package in which the openings are quickly and easily heat sealed by conduction after blood has been introduced into the cavity of the package.

It has long been recognized by personnel connected with the medical and nursing professions that a handy form of package for storing blood for long periods of time is a practical necessity. The discovery that additives such as glycerine can prevent blood cells from becoming damaged when frozen for a long period has increased the demand for suitable packaging.

Ideally, such a package should be provided which is flexible, durable, chemically resistant to its contents, and able to withstand rapid variations along a broad temperature range from, for example, $-200°$ C during freezing to $+200°$ C during sterilization. The material from which the package is formed should be as thin as possible, without losing its strength or durability, so that the contents can be rapidly refrigerated and defrozen. Moreover, equally as important as its physical characteristics, the package after it is filled should be able to be effectively sealed in a quick and uncomplicated way without having to use elaborate and expensive equipment.

Many different types of packaging for storing blood have been developed, but they all include conventional means for sealing the blood within the package, such as cap, plug, or a clamp or the like which are used in conjunction with a port or opening in the package. Seals effected in this way are undesirable in that they are susceptible to being broken if the elements forming the seal are accidently jarred. Blood packages are quite often subjected to less than desirable handling conditions, for example, in military operations, and a tight seal is of primary importance.

Using mechanical refrigeration techniques, temperatures as low as about $-80°$ C can be used, but such procedures require that higher concentrations of glycerol be mixed with the blood in order to protect the red cells. Down as low as $-130°$ C ice crystals may form in the blood which would cause destruction of the cells. Liquid nitrogen cools to temperatures of about $-196°$ C, and at that temperature about 100 mls of protective solution such as glycerol for each 250 ml of red blood cells are used. This is to be contrasted with 400 ml of such protective solution which is required per 250 ml of red blood cells, in the case of mechanical refrigeration at $-80°$ C.

When deep frozen, white cells are damaged. Some at $-80°$ C and even more at $-196°$ C. These, however, can be washed out. Aluminum vessels have been used for this operation and later stainless steel was used, but such metals are not suitable for centrifugation. They obviously are not transparent and so the operator cannot observe for contaminants. To meet this problem a plastic transparent bag has been sought for many years. Polyvinylchloride has been used at temperatures of $-4°$ C but at lower temperatures such as those mentioned above maintained by mechanical refrigeration ($-80°$ C), the PVC is brittle. PVC cannot be used at all at $-196°$ C because it is much too brittle.

An object of the invention, therefore, is to obtain a package containing a suspension of cellular components of blood which can be used for washing and centrifuging such suspension, as well as sterilizing and deep freezing the suspension, all in the same package.

SUMMARY OF THE INVENTION

There is provided, in accordance with the invention, a package for storing blood or a suspension of cellular components of the blood, such as red cells, white cells and/or platelets, which fulfills all the requirements mentioned above. The package is formed of a plastic laminate which defines an inner cavity, and at least one sealable opening leads to the cavity.

The laminate includes an inner layer which is adjacent to the cavity and formed of a fluorinated ethylene-propylene polymer such as tetrafluoroethylene-hexafluoro-propylene polymer. A suitable material for use in the package is marketed by DuPont and sold under the trademark Teflon FEP. The outer layer of the laminate, which is the durable wear resistant outer layer of the package, is formed of a non-thermoplastic polyimide. A suitable polyimide that can be used is made from the poly-condensation reaction between pyromellitic dianhydride and aromatic diamine. Such a polyimide is known as Kapton-Type H and is marketed by DuPont. In its preferred embodiment the laminate is a pre-formed, two-layer composite marketed under the trademark Kapton/Teflon-FEP, from which the packages are fabricated.

For effecting a satisfactory seal around the opening, the inner layer should be able to withstand temperatures up to at least about $+200°$ C and the outer layer should be able to withstand temperatures up to at least about $+400°$ C. To enable the blood cavity to be refrigerated and defrozen as quickly as possible and to effect a rapid sealing of the inner layers together the thickness of the laminate should range from about 0.05 mm. to about 0.5 mm.

Also in accordance with the invention, a method for storing blood in conjunction with such a package is provided. A package such as that described above is formed of the laminate, blood is then introduced into the cavity through the opening, and heat is applied thereafter by conduction through the outer layer of the laminate on at least one side of the package near the opening, the heat being above the melting temperature of the inner layer and below the melting temperature of the outer layer, for melting and sealing together the opposing inner layers and thereby blocking the opening from the cavity and preventing the blood in the cavity from escaping through the opening.

For a better understanding of the invention, reference may be had to the following description of exemplary embodiment, taken in conjunction with the accompanying drawing in which.

DETAILED DESCRIPTION OF THE PREFERRED EMBODIMENT

Figure 1:
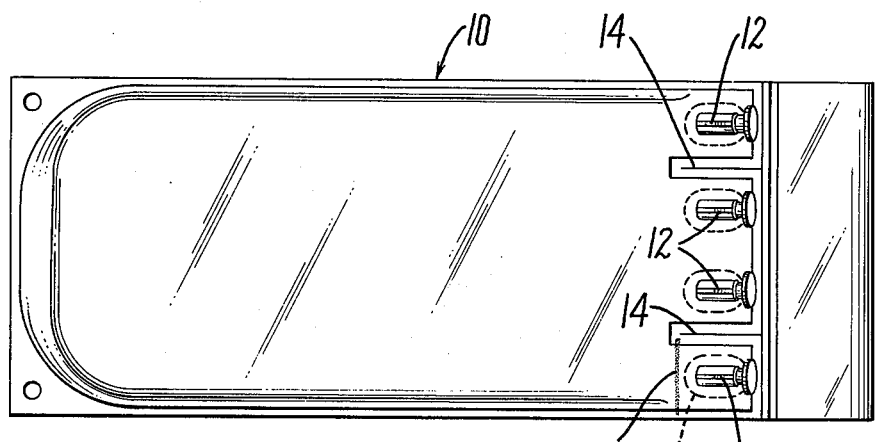
FIG. 1 is a top elevational view of the sealable package.
Figure 2:
FIG. 2 is a side elevational view of the sealable package.

Now, referring to FIGS. 1 and 2, the sealable package for storing blood is generally designated by reference numeral 10. The package 10 is formed of a two-layer laminate which defines an inner cavity (not shown). Leading to the cavity through the laminate are openings 12 through which blood can be introduced into the cavity or withdrawn therefrom. The initial fabrication of the package 10 can be accomplished in any known manner as long as an effective seal is provided around the edges of the package 10.

Adjacent the cavity is a layer of the laminate which will be called the inner layer and which necessarily must be formed of a material which is chemically inert with respect to blood. This layer is formed of a tetrafluoroethylene-hexafluoropropylene polymer. The particular material which is preferable for use in the package 10 is marketed by DuPont and known as Teflon FEP. Because the inner layer has relatively low strength characteristics it must be reinforced by a durable, wear resistant outer layer to resist the rough handling to which the package 10 may be put. The material having these latter properties that is used to form the outer layer is a non-thermoplastic polyimide. For use in the package 10, the preferable polymide used in the laminate is from the poly-condensation reaction between pyromellitic dianhydride and aromatic diamine. A suitable material for use in forming the outer layer is known as Kapton-Type H, which is marketed by DuPont. A more detailed description of this polyimide film can be found in the article, "H Film-A New High Temperature Dielectric," by Leonard E. Amborski, *I. E.C. Product Research and Development*, vol. 2, no. 3, Sept. 1963, pp. 189–193. This article is cited in U.S. Pat. No. 3,425,865, the application for which was filed on June 29, 1965, and which issued on Feb. 4, 1969, which discusses in detail other polyimides that may be used in the laminate described above.

In addition, a laminate including similar inner and outer layers may be provided that includes a greater number than the described two layers. However, the layer formed of the fluorinated ethylene-propylene polymer must always be adjacent to the cavity.

The laminate can withstand a rapid change along a broad temperature range. With the discovery that additives such as glycerine can increase the length of time that blood can safely remain frozen without any accompanying cell damage, there has been a great demand for blood packages to be used with rapid freezing techniques, for example, the use of liquid nitrogen, as well as being able to endure the high temperatures (about +180° C) during sterilization. The laminate described above has been found particularly suited to such use because of the ability of both layers to withstand temperatures from about −200° to about +200° C which covers the full range of freezing and sterilization.

The outer layer of the laminate, moreover, it able to withstand temperatures substantially higher than the inner layer, to at least about +400° C. In addition, the width of the two-layer laminate is relatively thin ranging from 0.05 mm. to about 0.5 mm., without sacrificing any of the strength or durability of the package 10, which is thought to be one of the primary reasons for the unique way that the inner layer can be sealed together by means of heat being applied through the outer layers, and which enables blood in the package 10 to be rapidly refrigerated or defrozen.

In operation, the package 10 is provided which is formed of the laminate material described above and fabricated of the pre-formed material by any known method. The package is completely closed and includes the openings 12, each of which can be used either as an inlet opening or an outlet opening and which are initially sealed in any suitable way, such as by pieces of plastic material being heat welded to the inner layer on its inner side as designated by broken lines 13 in FIG. 1. The seals can be broken by catheters (not shown) or the like through which the blood can be introduced or withdrawn from the cavity of the package 10 by known methods.

In its empty state, the package 10 is normally sterilized and then filled with blood through one of the openings 12. After the package 10 is filled the opening 12 through which the blood has been introduced is sealed shut by applying heat around the opening 12 through the outer layer on at least one side of the package for melting and heat welding together the opposing inner layers. A heating element (not shown) of any suitable design would normally be used to apply the heat. The heating element would have at least one heating surface which is movable into and out of clamping relationship with the package 10. Preferably, the temperature of the heat would be between the melting temperatures of the two layers, as described above, for preventing the outer layer from sticking to the heating element.

When the package 10 is fabricated a pre-sealed portion 14 can be provided between adjacent openings 12, forming a channel that can easily be sealed. To seal the opening 12, the heating element would clamp the package 10 on opposite sides and the heat would be applied through the outer layer on at least one side of the package and would melt the inner layers and seal them together. The seal which is the shaded portion in FIG. 1 designated by numeral 16 can assume any suitable shape, even entirely surrounding the opening 12, as long as it effectively blocks the opening 12 from the remaining portion of the cavity to prevent the blood from escaping through that opening 12. In this way, a fast and simple way of sealing the package 10, after it has been filled with blood, is provided.

The package 10 described in accordance with the invention can be used for the complete process of handling blood, from the moment of deep-freezing, through storage and de-freezing up to the amount of administering the transfusion. Because the package 10 is formed of a sufficiently strong material other intermediate treatment stages may also be used in conjunction with package 10, such as washing and centrifuging the blood.

Further, a plastic pocket may be provided on the outside of the package for attaching suitable labels which identify the contents of the package without disturbing the refrigerating or de-freezing process. In this connection, the plastic pocket is suitably designed so that it can be sealed against the ingress of water. In this way it is possible, for instance, to de-freeze the blood in the package in a water bath without the label becoming detached.

Another feature of the invention is that by heat welding, as described above with regard to the seal 16, separate smaller cavities for storing small amounts of blood may be provided in a portion of the package, whereby small amounts of blood may be removed from their separate portions to be used in laboratory tests, making it possible to conduct an analysis of the blood in the package 10 in a simple and uncomplicated manner.

Thus, there is provided in accordance with the invention a novel and improved package for storing blood and a method for storing blood in such a package. The embodiment of the invention described above is intended to be merely exemplary, and those skilled in the art will be able to make numerous variations and modifications, in addition to those mentioned above, without departing from the spirit and scope of the invention.

I claim:

1. A sealed package containing a stored suspension of cellular components of blood, said package comprising nonrigid laminate wall portions resistant to a temperature of approximately that of liquid nitrogen, said walls being formed of a plastic laminate and defining an inner cavity containing said suspension, with at least one sealed opening to the inner cavity, the laminate including an inner layer next to the cavity and the suspension therein formed of a heat sealable, fluorinated ethylenepropylene polymer and further including an outer layer formed of a nonthermoplastic polyimide which as a melting temperature substantially higher than that of the inner layer so as to withstand heat-sealing temperatures applied directly thereto which actuate and thereby heat-seal said inner layer.

2. A sealed package containing a suspension therein in accordance with claim 1, wherein the inner layer can withstand temperatures up to about 200° C and the outer layer can withstand temperatures up to at least 400° C.

3. A sealed package as described in claim 1, wherein the thickness of the laminate material ranges from 0.05 to about 0.5 mm.

4. A sealed package as described in claim 1, wherein the inner layer of the laminate material is Teflon.

5. A sealable package for storing a suspension in accordance with claim 1 in which said suspension comprises an additive to increase the time that the blood components can be frozen without cell damage.

6. A sealable package in accordance with claim 5 in which said additive is glycerine.

* * * * *

UNITED STATES PATENT AND TRADEMARK OFFICE
CERTIFICATE OF CORRECTION

PATENT NO. : 3,942,529
DATED      : March 9, 1976
INVENTOR(S) : Bard Meier Waage It is certified that error appears in the above-identified patent and that said Letters Patent are hereby corrected as shown below:

Col. 1, line 40, before "cap" insert --a--;

Col. 3, line 36, before "E.C." insert --&--;

Col. 3, line 60, "it" should read --is--;

Col. 4, line 49, "amount" should read --moment--;

Col. 6, line 1, "ethylenepropylene" should read --ethylene-propylene--; and

Col. 6, line 3, "as" should read --has--.

Signed and Sealed this fifteenth Day of June 1976

[SEAL]

Attest:

RUTH C. MASON
Attesting Officer

C. MARSHALL DANN
Commissioner of Patents and Trademarks